(12) United States Patent
Boukhny et al.

(10) Patent No.: US 8,684,145 B2
(45) Date of Patent: Apr. 1, 2014

(54) SYSTEMS AND METHODS FOR CONSOLE BRAKING

(75) Inventors: Mikhail Boukhny, Laguna Niguel, CA (US); David A. Thoe, Laguna Hills, CA (US); John Koontz, Corona, CA (US); Long Q. Nguyen, Tustin, CA (US); Scott B. Newton, Costa Mesa, CA (US); Daniel Bauen, Atlanta, GA (US); Cassilyn Bair, Atlanta, GA (US); Lawrence E. Davis, Atlanta, GA (US)

(73) Assignee: Alcon Research, Ltd., Fort Worth, TX (US)

( * ) Notice: Subject to any disclaimer, the term of this patent is extended or adjusted under 35 U.S.C. 154(b) by 300 days.

(21) Appl. No.: 13/017,102

(22) Filed: Jan. 31, 2011

(65) Prior Publication Data
US 2011/0247903 A1 Oct. 13, 2011

Related U.S. Application Data

(60) Provisional application No. 61/321,621, filed on Apr. 7, 2010.

(51) Int. Cl.
*F16D 63/00* (2006.01)

(52) U.S. Cl.
USPC .................... 188/68; 16/35 R; 312/351.13

(58) Field of Classification Search
USPC ............ 188/68–69, 17, 31, 2 F, 19, 156, 158, 188/161; 16/35 R; 312/351.13
See application file for complete search history.

(56) References Cited

U.S. PATENT DOCUMENTS

| | | | |
|---|---|---|---|
| 2,351,997 A * | 6/1944 | Morrill | .......................... 477/23 |
| 2,450,062 A | 9/1948 | Voss et al. | |
| 3,239,872 A | 3/1966 | Kitrell | |
| 3,652,103 A | 3/1972 | Higgs | |
| 3,818,542 A | 6/1974 | Jones | |
| 3,890,668 A | 6/1975 | Stosberg et al. | |
| 3,920,014 A | 11/1975 | Banko | |

(Continued)

FOREIGN PATENT DOCUMENTS

| | | |
|---|---|---|
| CH | 223517 A | 9/1942 |
| CN | 2273269 | 1/1998 |

(Continued)

OTHER PUBLICATIONS

International Searching Authority, Written Opinion of the International Searching Authority, International Application No. PCT/US2011/023107, Mar. 31, 2011, 7 pages.

(Continued)

*Primary Examiner* — Anna Momper

(57) ABSTRACT

In various embodiments, a braking system may include an actuator, a pawl gear coupled to the actuator, and a wheel gear plate. The braking system may further include a brake pad, an outer wheel coupled to the brake pad, and a spring washer plate configured to press the wheel gear plate against the brake pad such that the wheel gear plate is configured to inhibit rotation of the outer wheel through friction between the wheel gear plate and the brake pad when the pawl gear inhibits rotation of the wheel gear plate. In some embodiments, the braking system may further include a sensor and the actuator may be triggered to actuate the pawl gear in response to signals from the sensor.

17 Claims, 8 Drawing Sheets

(56) References Cited

U.S. PATENT DOCUMENTS

| | | |
|---|---|---|
| 4,025,099 A | 5/1977 | Virden |
| 4,110,866 A | 9/1978 | Ishii |
| 4,143,442 A | 3/1979 | Harlang |
| 4,467,496 A | 8/1984 | Gregg |
| 4,550,221 A | 10/1985 | Mabusth |
| 4,550,808 A | 11/1985 | Folson |
| 4,616,888 A | 10/1986 | Peterman |
| 4,633,544 A | 1/1987 | Hicks |
| 4,669,580 A | 6/1987 | Neville |
| 4,675,485 A | 6/1987 | Paukert |
| 4,677,706 A | 7/1987 | Screen |
| 4,744,536 A | 5/1988 | Bancalari |
| 4,811,966 A | 3/1989 | Singleton |
| 4,941,552 A | 7/1990 | Screen |
| 5,046,534 A * | 9/1991 | Vandenbroucke et al. ... 139/336 |
| D325,086 S | 3/1992 | Charles et al. |
| 5,112,019 A | 5/1992 | Metzler et al. |
| 5,242,035 A | 9/1993 | Lange |
| 5,249,121 A | 9/1993 | Baum et al. |
| 5,273,043 A | 12/1993 | Ruike |
| 5,315,290 A | 5/1994 | Moreno et al. |
| D352,106 S | 11/1994 | Fanney et al. |
| 5,456,336 A | 10/1995 | Bopp |
| 5,624,352 A * | 4/1997 | Smale ........................... 477/197 |
| 5,650,597 A | 7/1997 | Redmayne |
| 5,655,542 A | 8/1997 | Weilandt |
| 5,702,117 A | 12/1997 | Geelhoed |
| 5,766,146 A | 6/1998 | Barwick, Jr. |
| 5,788,651 A | 8/1998 | Weilandt |
| 5,788,688 A | 8/1998 | Bauer et al. |
| 5,794,639 A * | 8/1998 | Einbinder ....................... 135/67 |
| 5,800,383 A | 9/1998 | Chandler et al. |
| 5,810,765 A | 9/1998 | Oda |
| 5,823,302 A | 10/1998 | Schweninger |
| 5,827,146 A | 10/1998 | Yan et al. |
| 5,827,149 A | 10/1998 | Sponable |
| 5,830,180 A | 11/1998 | Chandler et al. |
| 5,857,685 A | 1/1999 | Phillips et al. |
| 5,859,629 A | 1/1999 | Tognazzini |
| 5,876,016 A | 3/1999 | Urban et al. |
| 5,880,538 A | 3/1999 | Schulz |
| 5,964,313 A | 10/1999 | Guy |
| 5,988,323 A | 11/1999 | Chu |
| 6,024,720 A | 2/2000 | Chandler et al. |
| 6,034,449 A | 3/2000 | Sakai et al. |
| 6,047,634 A | 4/2000 | Futsuhara et al. |
| 6,055,458 A | 4/2000 | Cochran et al. |
| 6,109,572 A | 8/2000 | Urban et al. |
| 6,126,617 A | 10/2000 | Weilandt et al. |
| 6,232,758 B1 | 5/2001 | Konda et al. |
| 6,251,113 B1 | 6/2001 | Appelbaum et al. |
| 6,276,485 B1 | 8/2001 | Eriksson et al. |
| D447,567 S | 9/2001 | Murphy et al. |
| 6,322,523 B2 | 11/2001 | Weilandt et al. |
| 6,357,765 B1 | 3/2002 | Heien |
| 6,409,187 B1 | 6/2002 | Crow, Jr. |
| 6,429,782 B2 | 8/2002 | Pavatich et al. |
| D467,001 S | 12/2002 | Buczek et al. |
| 6,501,198 B2 | 12/2002 | Taylor et al. |
| 6,503,208 B1 | 1/2003 | Skovlund |
| 6,520,929 B2 | 2/2003 | Zaleski |
| 6,530,598 B1 | 3/2003 | Kirby |
| 6,532,624 B1 | 3/2003 | Yang |
| 6,587,750 B2 | 7/2003 | Gerbi et al. |
| 6,590,171 B1 | 7/2003 | Wolf et al. |
| 6,619,438 B1 | 9/2003 | Yang |
| 6,626,445 B2 | 9/2003 | Murphy et al. |
| 6,662,404 B1 | 12/2003 | Stroh et al. |
| 6,678,917 B1 | 1/2004 | Winters et al. |
| 6,749,538 B2 | 6/2004 | Slawinski et al. |
| 6,824,539 B2 | 11/2004 | Novak |
| 6,854,568 B2 | 2/2005 | Kun-Tsai |
| 6,944,910 B2 | 9/2005 | Pauls |
| 6,969,032 B2 | 11/2005 | Olivera et al. |
| 6,971,617 B2 | 12/2005 | Nguyen et al. |
| 7,036,185 B2 | 5/2006 | Morndal et al. |
| 7,065,812 B2 | 6/2006 | Newkirk et al. |
| 7,100,716 B2 | 9/2006 | Engels et al. |
| D550,362 S | 9/2007 | Olivera et al. |
| 7,454,839 B2 | 11/2008 | Della Bona et al. |
| 7,509,747 B2 | 3/2009 | Sudou et al. |
| 7,685,660 B2 | 3/2010 | Chinn |
| 7,708,120 B2 * | 5/2010 | Einbinder ....................... 188/31 |
| 7,878,289 B2 | 2/2011 | Standke |
| 7,986,525 B2 | 7/2011 | Wang |
| 8,015,666 B2 | 9/2011 | Wang |
| 8,060,982 B2 | 11/2011 | Magoz et al. |
| 2001/0023331 A1 | 9/2001 | Kanda et al. |
| 2004/0004331 A1 | 1/2004 | Pauls |
| 2004/0119484 A1 | 6/2004 | Basir et al. |
| 2004/0226187 A1 | 11/2004 | Bruntz et al. |
| 2005/0004559 A1 | 1/2005 | Quick et al. |
| 2005/0088417 A1 | 4/2005 | Mulligan |
| 2005/0230575 A1 | 10/2005 | Zelenski et al. |
| 2005/0234441 A1 | 10/2005 | Bisch et al. |
| 2006/0031989 A1 | 2/2006 | Graham et al. |
| 2006/0113733 A1 | 6/2006 | Kazaoka |
| 2006/0149426 A1 | 7/2006 | Unkrich et al. |
| 2006/0267295 A1 | 11/2006 | You |
| 2007/0051566 A1 | 3/2007 | Marlow |
| 2007/0124858 A1 | 6/2007 | Ahlman |
| 2008/0033361 A1 | 2/2008 | Evans et al. |
| 2008/0114290 A1 | 5/2008 | King et al. |
| 2008/0126969 A1 | 5/2008 | Blomquist |
| 2008/0189173 A1 | 8/2008 | Bakar et al. |
| 2008/0223650 A1 | 9/2008 | Standke |
| 2009/0036271 A1 | 2/2009 | Brand et al. |
| 2009/0040181 A1 | 2/2009 | Darnell et al. |
| 2009/0045021 A1 | 2/2009 | Einbinder |
| 2009/0069799 A1 | 3/2009 | Daw et al. |
| 2009/0090434 A1 | 4/2009 | Brand et al. |
| 2009/0143734 A1 | 6/2009 | Humayun et al. |
| 2009/0231095 A1 | 9/2009 | Gray |
| 2009/0289431 A1 | 11/2009 | Geeslin |
| 2010/0049119 A1 | 2/2010 | Norman et al. |
| 2010/0058557 A1 | 3/2010 | Wang |
| 2011/0247173 A1 | 10/2011 | Nguyen et al. |
| 2011/0251548 A1 | 10/2011 | Koontz et al. |

FOREIGN PATENT DOCUMENTS

| | | |
|---|---|---|
| CN | 2273269 Y | 1/1998 |
| DE | 2102508 B2 | 6/1973 |
| DE | 3016615 A1 | 11/1981 |
| DE | 3039611 A1 | 4/1982 |
| DE | 3203886 A1 | 9/1983 |
| DE | 8910606 U1 | 10/1989 |
| DE | 4344187 A1 | 6/1995 |
| DE | 19504073 C1 | 8/1996 |
| DE | 19620059 A1 | 11/1997 |
| DE | 10047006 C2 | 4/2002 |
| DE | 20308670 U1 | 2/2004 |
| DE | 10332823 A1 | 2/2005 |
| DE | 202005016310 U1 | 1/2006 |
| DE | 202007008797 U1 | 8/2007 |
| DE | 102006049071 B3 | 11/2007 |
| DE | 102008015505 A1 | 2/2009 |
| DE | 102007053444 A1 | 5/2009 |
| DE | 102009058919 A1 | 6/2011 |
| EP | 0701917 A1 | 3/1996 |
| EP | 0865055 A1 | 9/1998 |
| EP | 0979741 A2 | 2/2000 |
| EP | 1016580 A1 | 7/2000 |
| EP | 1024071 A1 | 8/2000 |
| EP | 1180473 A1 | 2/2002 |
| EP | 0901388 B1 | 1/2003 |
| EP | 1964750 A1 | 9/2008 |
| EP | 2106986 A1 | 10/2009 |
| EP | 1016578 B1 | 3/2010 |
| EP | 2173154 B1 | 1/2011 |
| EP | 2292202 A2 | 3/2011 |
| ES | 2285964 | 11/2007 |
| FR | 2648101 | 12/1990 |
| FR | 2799410 A1 | 4/2001 |

(56) References Cited

FOREIGN PATENT DOCUMENTS

| | | | |
|---|---|---|---|
| FR | 2880700 A1 | 7/2006 | |
| GB | 210851 | 2/1924 | |
| GB | 767159 | 1/1957 | |
| GB | 2061105 | 5/1981 | |
| GB | 2132478 | 7/1984 | |
| GB | 2260195 A | 4/1993 | |
| GB | 2260622 A | 4/1993 | |
| GB | 2303675 A | * | 2/1997 |
| GB | 2441303 A | 3/2008 | |
| JP | 02-107245 | 4/1990 | |
| JP | 03-062902 | 3/1991 | |
| JP | 03-190919 | 8/1991 | |
| JP | 03-252266 | 11/1991 | |
| JP | 04-063328 | 2/1992 | |
| JP | 09-058203 | 3/1997 | |
| JP | 09-113071 | 5/1997 | |
| JP | 10-297206 | 11/1998 | |
| JP | 11-169411 | 6/1999 | |
| JP | 11-244339 | 9/1999 | |
| JP | 2001-001703 | 1/2001 | |
| JP | 2001-058503 | 3/2001 | |
| JP | 2003-220803 | 8/2003 | |
| JP | 2005-162113 | 6/2005 | |
| JP | 2005-296606 | 10/2005 | |
| JP | 2006-131198 A | 5/2006 | |
| JP | 2006-341670 | 12/2006 | |
| JP | 2007-137305 | 6/2007 | |
| JP | 2009-512971 | 3/2009 | |
| JP | 2010-508104 | 3/2010 | |
| JP | 2010-088490 | 4/2010 | |
| WO | 96/19143 A1 | 6/1996 | |
| WO | WO 98/25556 A1 | 6/1998 | |
| WO | WO 00/12150 A1 | 3/2000 | |
| WO | WO 00/18012 A1 | 3/2000 | |
| WO | 01/61431 A1 | 8/2001 | |
| WO | WO 02/043571 A2 | 6/2002 | |
| WO | WO 02/043571 A3 | 4/2003 | |
| WO | 03/068580 A1 | 8/2003 | |
| WO | WO 03/093408 A1 | 11/2003 | |
| WO | WO 2004/017521 A1 | 2/2004 | |
| WO | WO 2004/082554 A2 | 9/2004 | |
| WO | WO 2004/082554 A3 | 3/2005 | |
| WO | WO 2006/073400 A1 | 7/2006 | |
| WO | WO 2008/052752 A1 | 5/2008 | |
| WO | WO 2008/053485 A1 | 5/2008 | |
| WO | WO 2009/073691 A2 | 6/2009 | |
| WO | WO 2009/073769 A2 | 6/2009 | |
| WO | WO 2009/073691 A3 | 7/2009 | |
| WO | WO 2009/073769 A3 | 7/2009 | |
| WO | WO 2010/020200 A1 | 2/2010 | |
| WO | WO 2010/027255 A1 | 3/2010 | |
| WO | WO 2010/027255 A8 | 3/2010 | |
| WO | WO 2011/126596 A1 | 10/2011 | |
| WO | WO 2011/126597 A1 | 10/2011 | |
| WO | WO 2011/127231 A1 | 10/2011 | |

OTHER PUBLICATIONS

International Searching Authority, International Search Report, International Application No. PCT/US2011/023107, Mar. 31, 2011, 2 pages.
International Searching Authority, International Search Report, International Application No. PCT/US11/23103, Mar. 30, 2011, 2 pages.
International Searching Authority, Written Opinion of the International Searching Authority, International Application No. PCT/US11/23103, Mar. 30, 2011, 4 pages.
International Searching Authority, International Search Report, PCT/US2011/031500, Jun. 16, 2011, 2 pages.
International Searching Authority, Written Opinion of the International Searching Authority, PCT/US2011/031500, Jun. 16, 2011, 6 pages.
Steinco brochure accessed through http://web.archive.org/web/20080731183316/http://www.steinco.de/service/downloads.aspx?id=6901 & accessed from page http://web.archive.org/web/20080731183316/http://www.steinco.de/en/Castors_Hospital.aspx—original date believed to be Jul. 31, 2008, 2 pages.
http://web.archive.org/web/20090526022232/http://www.touchsensor.com/engineers.html?bcsi_scan_0A8B7FA59D377CC3=w1 . . . (web archive dated May 26, 2009) (2 pages).
http://web.archive.org/web/20090322184659/http://www.touchsensor.com/technology_switch.html (web archive dated Mar. 22, 2009) (2 pages).
European Patent Office, Extended European Search Report, EP 11766297.3, Jul. 31, 2013, 7 pages.

* cited by examiner

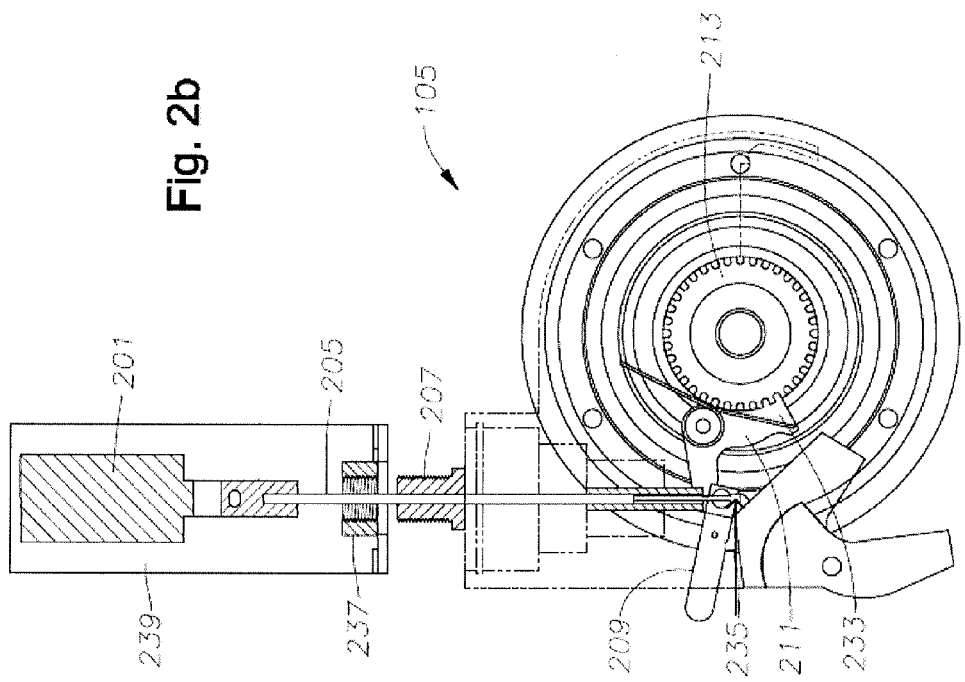
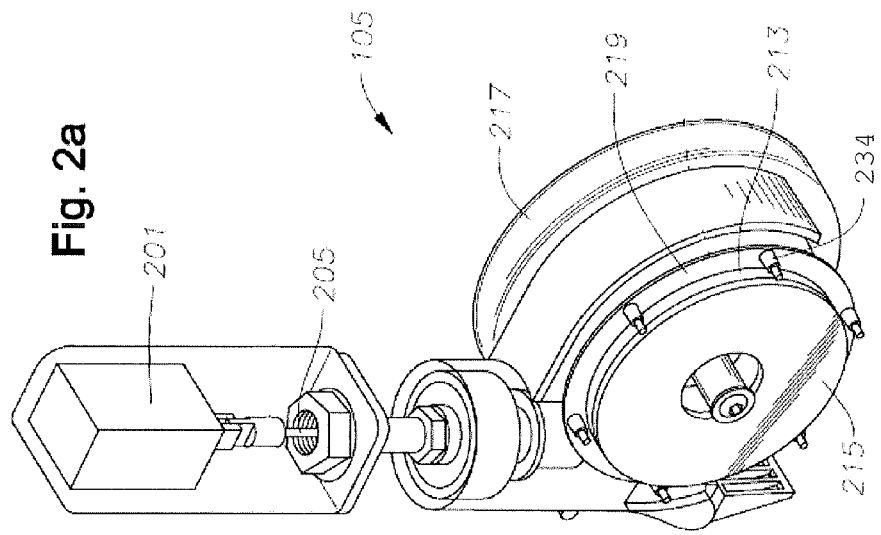

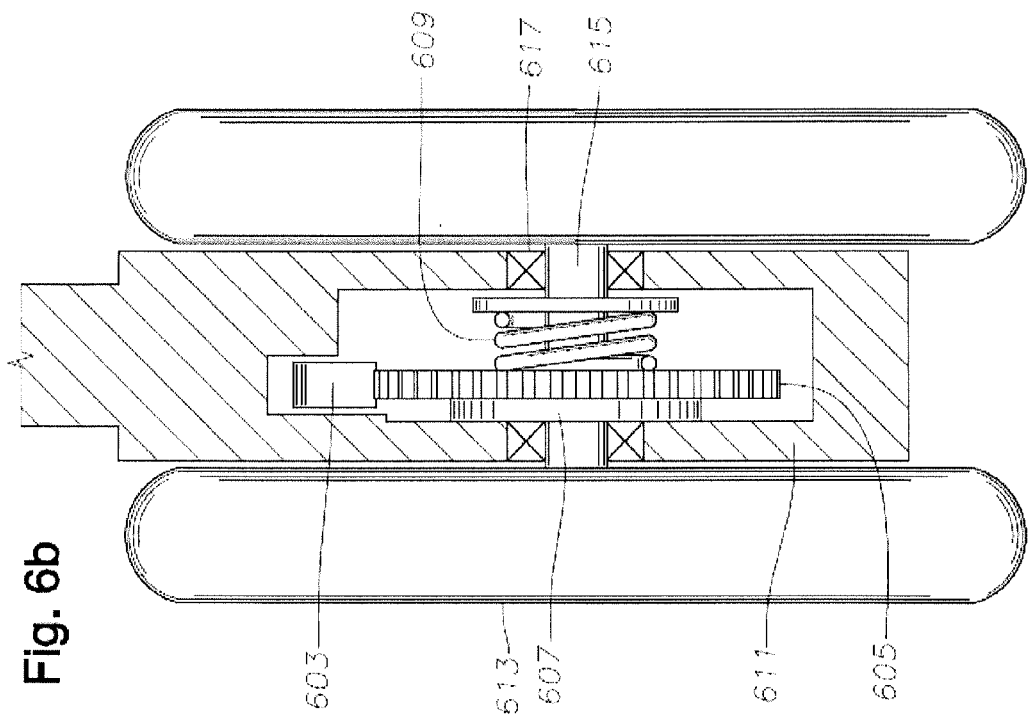
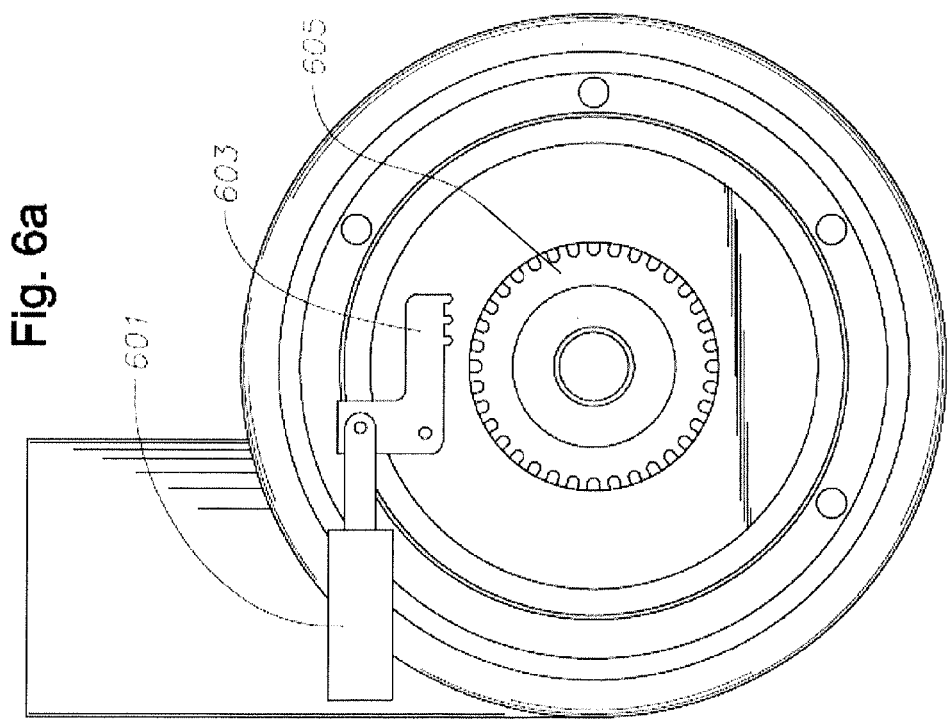

SYSTEMS AND METHODS FOR CONSOLE BRAKING

PRIORITY CLAIM

This application claims the benefit of priority of U.S. Provisional Patent Application Ser. No. 61/321,621 titled "Systems and Methods for Console Braking", filed on Apr. 7, 2010, whose inventors are Long Q. Nguyen, John Koontz, David A. Thoe, Mikhail Boukhny, Scott B. Newton, Daniel Bauen, Cassilyn Bair, and Lawrence E. Davis, which is hereby incorporated by reference in its entirety as though fully and completely set forth herein.

FIELD OF THE INVENTION

The present invention generally pertains to wheel control. More particularly, but not by way of limitation, the present invention pertains to wheel braking.

DESCRIPTION OF THE RELATED ART

Many previous casters use levers to individually lock/unlock wheels (e.g., on a console). A console user may move a lever by using their foot or by reaching down and moving the lever with their finger to lock or unlock the caster wheel. These manual level casters may be time consuming to engage/disengage and may make it difficult to determine a lock/unlock status of each wheel. Further, the casters may not provide emergency braking should braking be needed while the console is moving (e.g., if the user should trip and let go of the console).

SUMMARY

In various embodiments, a braking system may include an actuator, a pawl gear coupled to the actuator, and a wheel gear plate. The braking system may further include a brake pad, an outer wheel coupled to the brake pad, and a spring washer plate configured to press the wheel gear plate against the brake pad. In some embodiments, the wheel gear plate may inhibit rotation of the outer wheel through friction between the wheel gear plate and the brake pad when the pawl gear inhibits rotation of the wheel gear plate. In some embodiments, the spring washer plate may be attached to the outer wheel.

In some embodiments, the braking system may further receive user input, for example, through screen inputs, a remote control, buttons on the console, or a sensor (e.g., a field effect or capacitive sensor). In some embodiments, the sensor may be located on a handle of the surgical console to detect a touch from a user (e.g., as the user grips the handle to move the console). The actuator may be triggered to actuate the pawl gear to release or inhibit rotation of the wheel gear plate in response to signals from the sensor. For example, the actuator may actuate the pawl gear to inhibit rotation of the wheel gear plate unless a touch is being detected through the sensor (e.g., to apply the brake during times the user is not grasping the handle). In some embodiments, the braking system may further include a manual lever coupled to the pawl gear and accessible to a user of the surgical console to allow the user to manually actuate the pawl gear to release or inhibit rotation of the main gear plate independent of the actuator.

BRIEF DESCRIPTION OF THE DRAWINGS

For a more complete understanding of the present invention, reference is made to the following description taken in conjunction with the accompanying drawings in which:

FIGS. 2a-c are cross sections of a caster of the braking system, according to an embodiment;

FIGS. 6a-b illustrate an alternate embodiment of the braking system caster; and

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
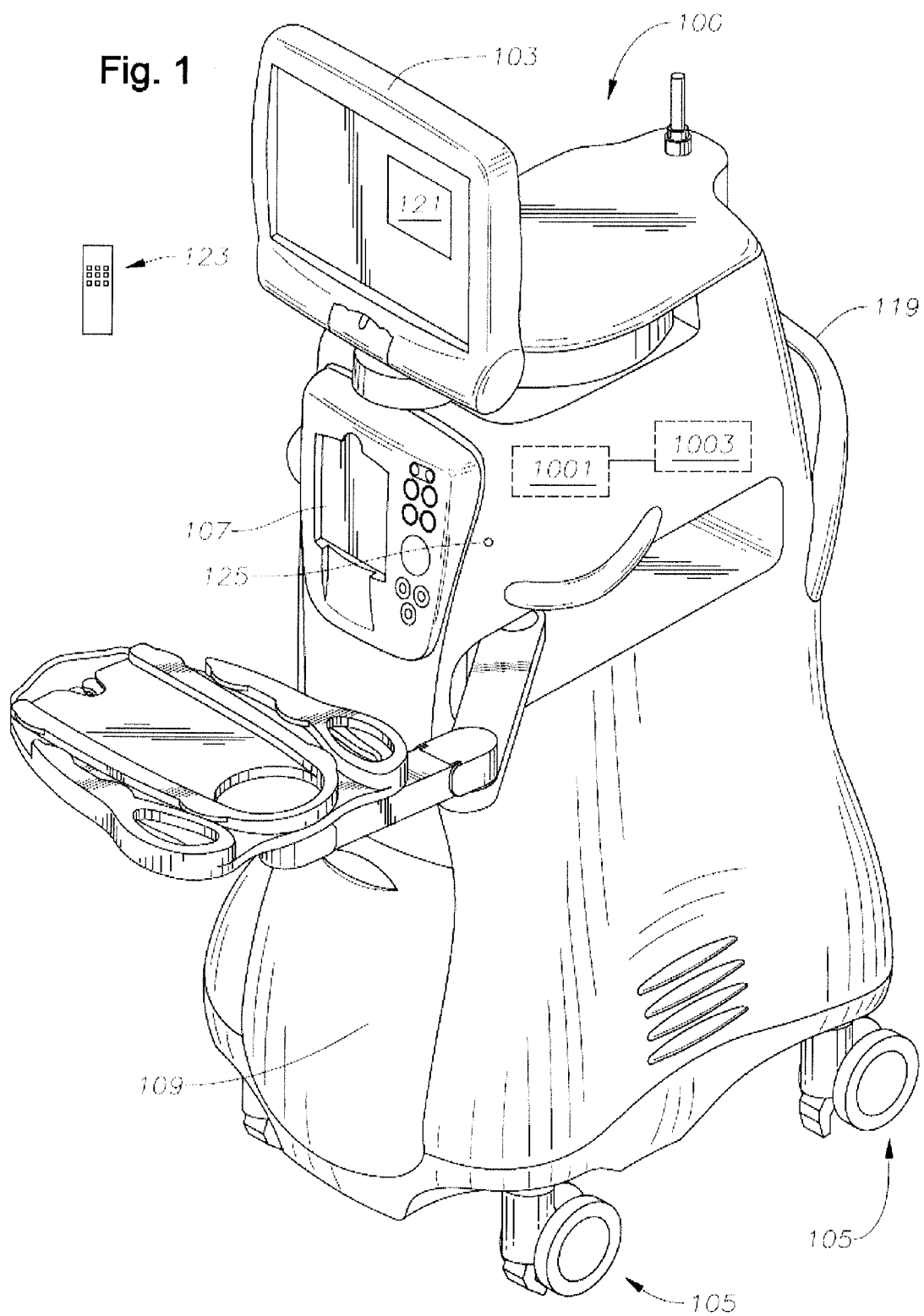
FIG. 1 is a surgical console implementing the braking system, according to an embodiment.

FIG. 1 is a surgical console implementing an embodiment of the braking system. In some embodiments, the surgical console 100 may include one or more casters 105 implementing a braking system to facilitate console movement and control. The casters 105 may provide automatic braking that, for example, automatically stops the console 100 when the console 100 is not being pushed/pulled by a user and automatically disengages when a user begins to push/pull the console 100. The braking system may also provide smooth braking to prevent the console 100 from tipping during the braking procedure. In some embodiments, the surgical console 100 may include, among other equipment, a touchscreen 103, fluidics cassette 107, handle 119, and auxiliary equipment bay 109. While braking casters 105 are disclosed herein with respect to a surgical console 100 for use in ophthalmic procedures, it is to be understood that the braking casters 105 may be used with other equipment carts and consoles.

Figure 2C:
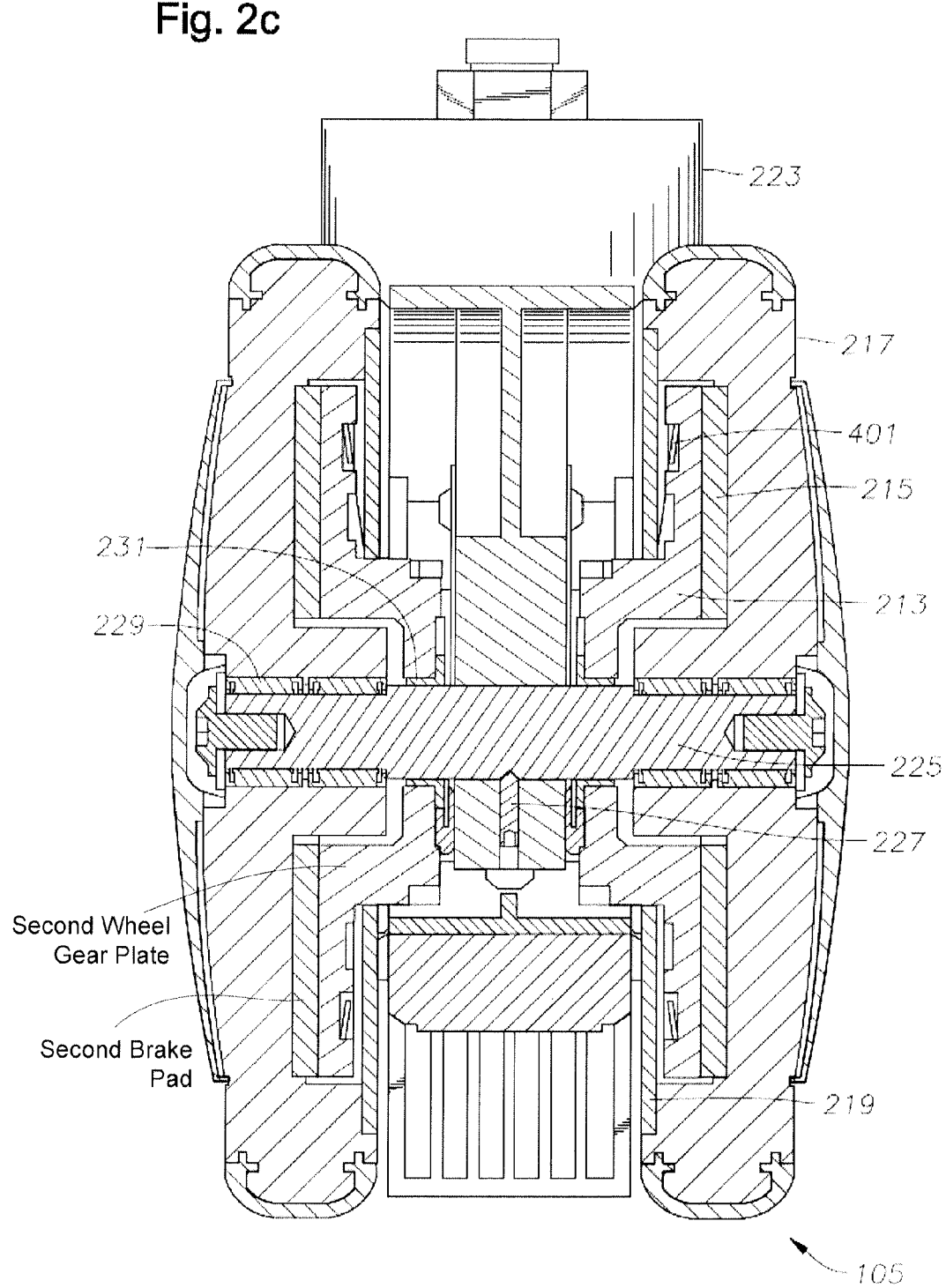
Figure 3:
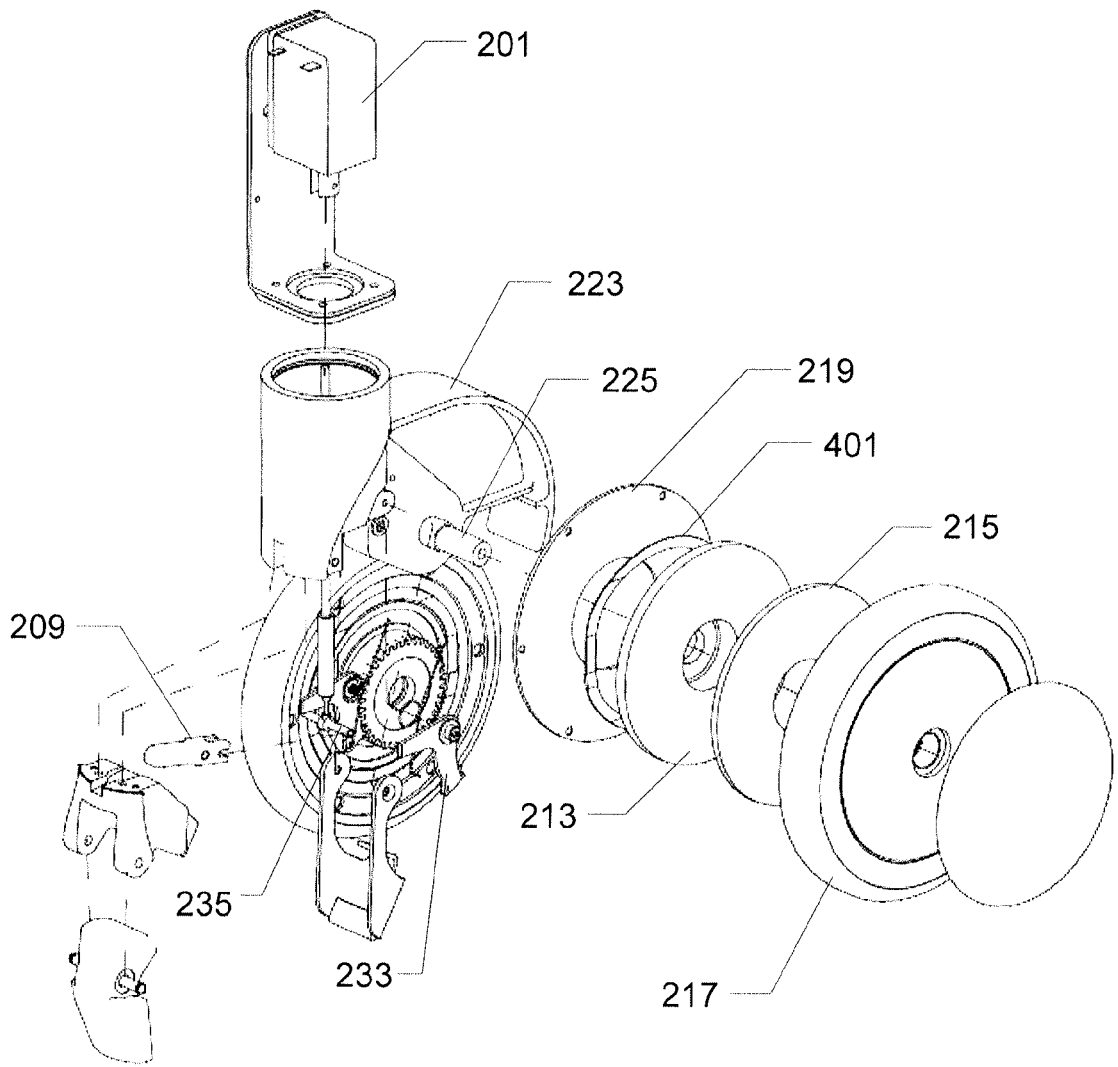
FIG. 3 is an exploded view of the caster of the braking system showing the brake pad, according to an embodiment.
Figure 4B:
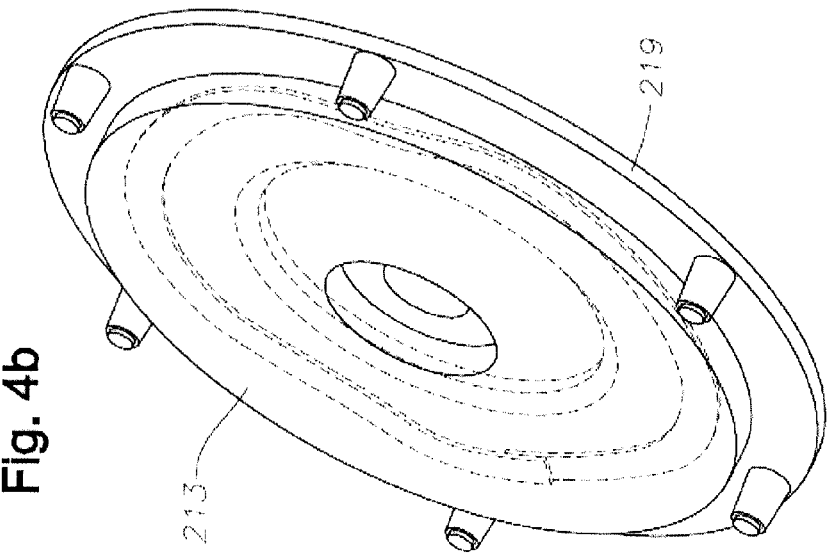
FIGS. 4a-c include views of the spring washer and wheel gear plate of the braking system, according to an embodiment.
Figure 4A:
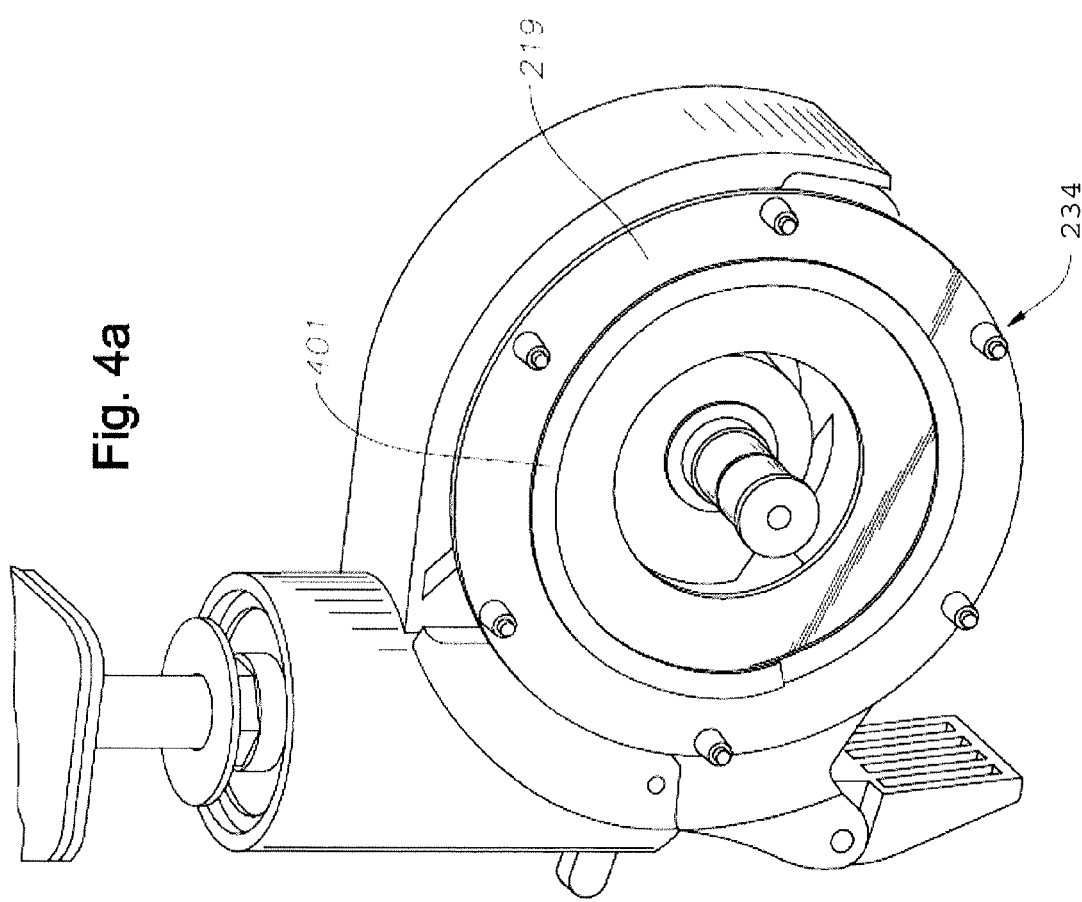
Figure 4C:
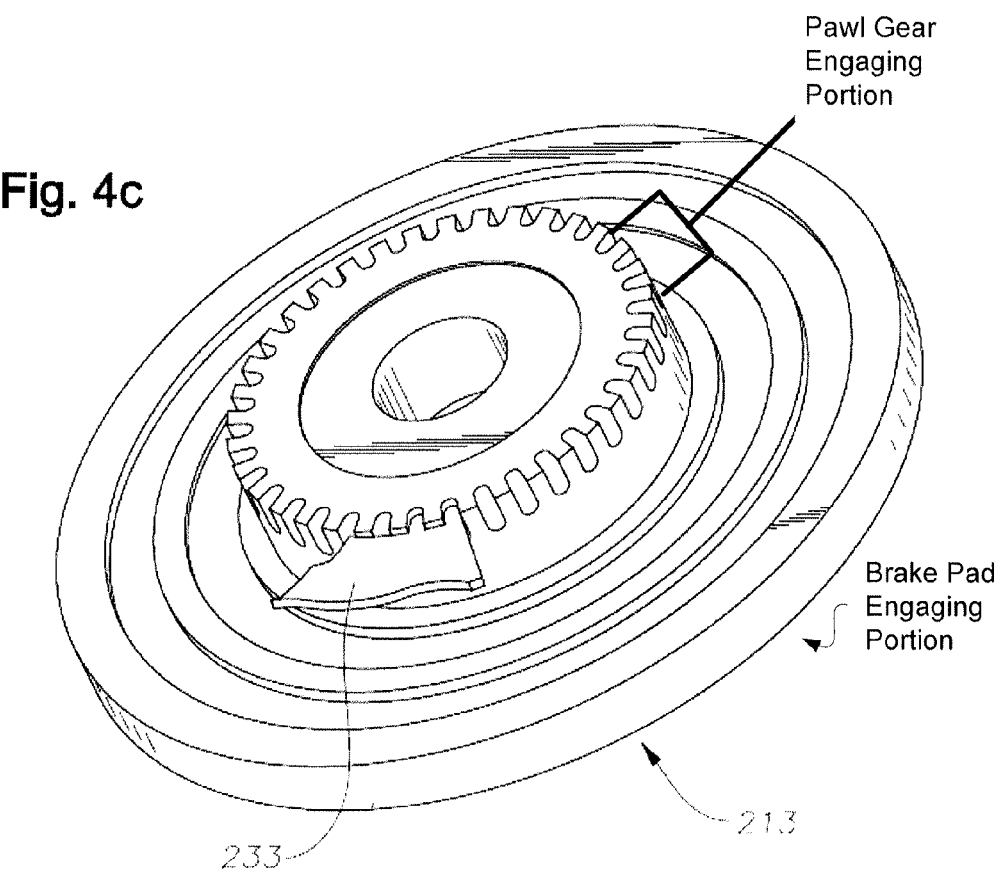

FIGS. 2a-c are cross sections of an embodiment of the braking caster 105, and FIG. 3 is an exploded view of an embodiment of the braking caster 105. The braking caster 105 may include one or more wheel gear plates 213 that include a brake pad engaging section and an inner pawl gear engaging section (see also FIG. 4c). The inner pawl gear engaging section may include a set of teeth along the circumference thereof to engage one or more teeth on a pawl gear 233. Rotation of the wheel gear plate 213 may be inhibited by engagement with the pawl gear 233. In some embodiments, the wheel gear plate 213 may be pressed against a brake pad 215 by a spring washer plate 219. For example, a circular spring washer 401 may press the wheel gear plate 213 into the brake pad 215. The circular spring washer 401 may be a resilient circular steel spring (other materials and configurations are also possible). As seen in FIG. 4a, the spring washer 401 may be attached (e.g., through an adhesive, friction fit, etc.) to the spring washer plate 219 which may itself be attached (e.g., through attachment points 234) or be part of the outer wheel 217. In some embodiments, the inner pawl gear 233 engaging section of the wheel gear plate 213 may fit through a hole in the spring washer plate 219 such that the inner pawl gear engaging section and the brake pad engaging section of the wheel gear plate 213 may be on opposing sides of the spring washer plate 219. The attachment points 234 may, for example, be snapped into, be glued to, or be molded into receiving portions of the outer wheel 217. Other attachments are also contemplated (e.g., the spring washer plate 219 and the outer wheel 217 may form a continuous piece). In some embodiments, the wheel gear plate 213, pawl gear 233 and spring washer plate 219 may be made of a suitable material such as metal or plastic.

In some embodiments, the brake pad 215 may be attached (e.g., through an adhesive) to the outer wheel 217. The brake pad 215 may be made of polyimide (or another material that provides resistance when engaged with the wheel gear plate 213). In some embodiments, the wheel gear plate 213 may be at least partially sandwiched between the brake pad 215 and the spring washer plate 219 such that when rotation of the wheel gear plate 213 is inhibited by engagement between the wheel gear plate 213 and the pawl gear 233, friction between the wheel gear plate 213 and the brake pad 215 may slow/stop the outer wheel 217. FIG. 4b illustrates another view of the contact between the wheel gear plate 213 and the spring washer plate 219. In an alternate embodiment, the brake pad 215 may be coupled to the wheel gear plate 213 such that friction between movement of the brake pad 215 relative to the outer wheel 217 may slow motion of the outer wheel 217.

In some embodiments, the pawl gear 233 may be part of a prong bracket 211 that positions the pawl gear 233 away or in engagement with the wheel gear plate 213. The prong bracket 211 may be in contact with a pin 235 that may itself be attached to a plunger rod 205. In some embodiments, the pawl gear may be directly attached to the pin 235 and/or plunger rod 205). As the plunger rod 205 moves up and down along a shaft of the wheel (e.g., at least partially running through a threaded stud 207), the pin 235 may move up and down. Movement of the pin 235 may move the prong bracket 211 up and down which may result in either engagement or disengagement of the pawl gear 233 with the wheel gear plate 213 through rotation of the prong bracket 211/pawl gear 233 relative to the pin 235. The pin 235 may include a separate pin or may include a connection (e.g., an adhesive) between the plunger rod 205 and the prong bracket 211). Other pin configurations are also possible. In some embodiments, an actuator 201 may be triggered to move the plunger rod 205, through a linear translation, to cause movement of the pawl gear 233 (to cause the wheel to brake or allow the wheel to freely rotate). In some embodiments, the prong bracket 211/pawl gear 233 may move relative to the pin 235 other than through rotation (e.g., through linear movement) and the plunder rod 205 may move via the actuator 201 through other than linear movement (e.g., through rotation). Other relative movements are also possible. In some embodiments, the actuator 201 may include a bi-stable solenoid that can hold either a lock or unlock position without power once engaged. The bi-stable solenoid may reduce power drain (e.g., if on battery power) and increase the flexibility of setting transportation modes. Other actuators are also contemplated. For example, the actuator 201 may be a pneumatic actuator, electrical relay, piezoelectric actuator, screw actuator, etc.

In some embodiments, housing 239 may surround the actuator 201 and interface the braking caster 105 with the surgical console 100. In FIGS. 2a-b, threaded stud 207 is shown uncoupled (e.g., unscrewed) from receiving stud nut 237. In use, the threaded stud 207 may be coupled (e.g., screwed) into stud nut 237 to form a secure connection between the housing 239 and the caster wheels 217.

As seen in FIG. 2c, each caster wheel 105 may include two outer wheels 217 each with their own wheel gear plate 213, spring washer plate 219, and brake pad 215. In some embodiments, the pawl gear 233 may be wide enough to engage the inner pawl gear engaging sections of both wheel gear plates 213 for a single caster 105. In some embodiments, two pawl gears 233 (one for each inner pawl gear engaging section) may be configured to move in unison (or as directed by the actuator 201). In some embodiments, only one side of the caster wheel 105 may include the wheel gear plate 213, spring washer plate 219, and brake pad 215. In some embodiments, the caster wheel 105 may include only one outer wheel 217 and that single outer wheel 217 may include the wheel gear plate 213, spring washer plate 219, and brake pad 215. Other configurations are also contemplated (e.g., a four wheel caster).

Also as seen in FIG. 2c, the outer wheels 217 may be connected through a central shaft 225. For example, the wheels 217 may be coupled to the shaft 225 through bearings 229 (which may be attached to the wheels through adhesive, a friction fit, etc. and may have a low-friction interface with the shaft 225). In some embodiments, one or more bushings 231 may be used between the wheel gear plate 213 and the shaft 225 to provide a low-friction interface between the wheel gear plate 213 and the shaft 225. In some embodiments, the shaft 225 may be coupled to the wheel housing 223 through a shaft screw 227 that may provide a fixed attachment between the wheel housing 223 and the shaft 225.

Figure 5:
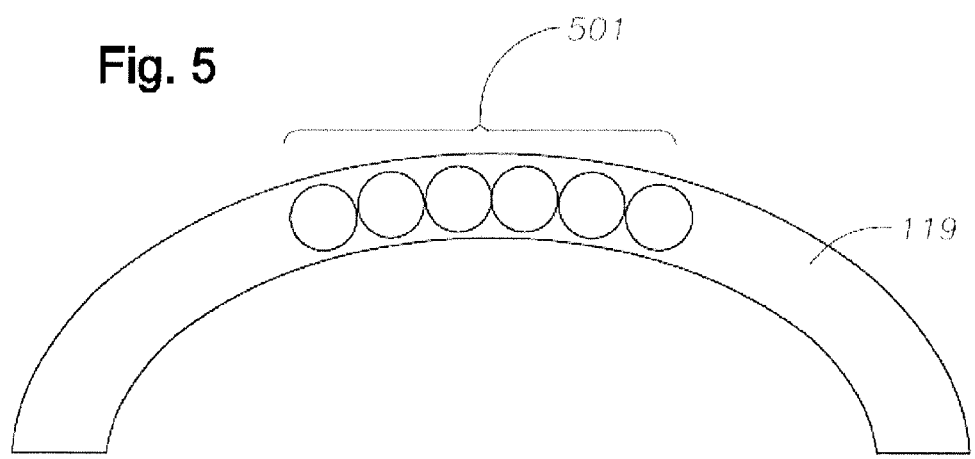
FIG. 5 illustrates a console handle and sensors, according to an embodiment.

In some embodiments, the braking system may further receive user input, for example, through touch screen inputs (e.g., through icon 121), a remote control 123, buttons 125 on the console 100, or a sensor (e.g., a field effect or capacitive sensor). As seen in FIG. 5, in some embodiments, the sensor 501 may be located on a handle 119 of the surgical console 100 to detect a touch from a user. The sensors 501 may be field effect switch sensors such as Touchcell™ sensors (e.g., which use low impedance electrodynamic field-effect technology) which may produce digital logic-level switching output. The field effect switch sensors may produce an electric field and detect a change in the electric field when a conductive mass (such as a human finger) enters the field. Other sensors (e.g., resistive sensors that can detect a user's presence are also contemplated). For example, the sensors may include cameras, infrared detectors, etc. In some embodiments, the sensor inputs may be used in controlling the actuator 201. For example, the actuator 201 may be signaled to release the wheel gear plate 213 (such as by lifting the pawl gear 233 out of engagement with the wheel gear plate 213) when user contact with the handle 119 is detected (indicating that a user is positioned to move the surgical console 100). In some embodiments, the pawl gear 233 may remain engaged with the wheel gear plate 213 when contact is not detected to prevent inadvertent movement of the surgical console 100 (e.g., through an inadvertent bump).

In some embodiments, a manual lock 209 may also be coupled to the pin 235 to provide a manual option to move the pawl gear 233 (through motion of the pin) into or out of engagement with the wheel gear plate 213. For example, a user may move the manual lock 209 to disengage the pawl gear 233 from the wheel gear plate 213 to allow the user to move the surgical console 100 (e.g., without necessarily touching the handle 119).

FIGS. 6a-b illustrate an alternate embodiment of the braking casters. The actuator (e.g., solenoid 601) may be located in line with the pawl gear 603. The pawl gear 603 may engage the wheel gear plate 605 to inhibit rotation of the wheel gear plate 605. The wheel gear plate 605 may be pressed against brake pad 607 via a spring 609 (shown in cross section through the spring coils). Brake pad 607 may in turn be pressed against inner housing 611. In some embodiments, the brake pad 607 may be attached to the inner housing 611 to provide friction between the surface of the brake pad 607 and the wheel gear plate 605 or the brake pad 607 may be attached to the wheel gear plate 605 to provide friction between the surface of the brake pad 607 and the inner housing 611. As further seen in FIG. 6*b*, the outer wheels 613 may be connected through a central shaft 615. For example, the wheels 613 may be coupled to the shaft 615 through bearings 617 (which may be attached to the wheels 613 through adhesive, a friction fit, etc. and may have a low-friction interface with the shaft 615).

Figure 7:
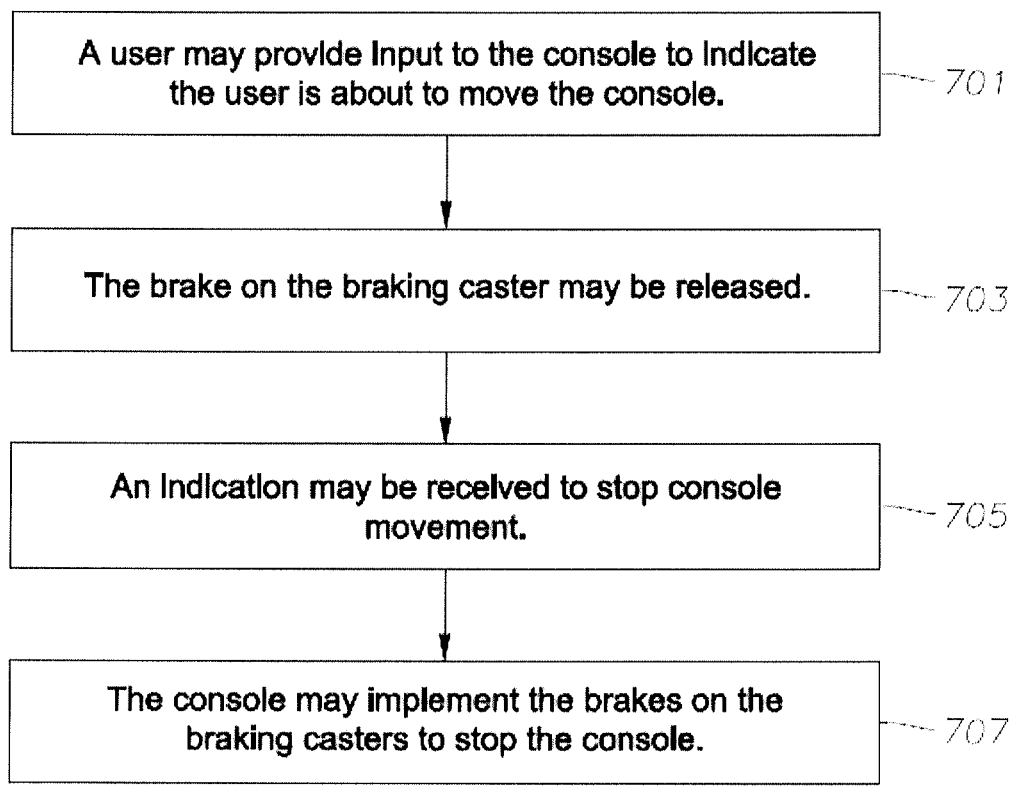
FIG. 7 illustrates a flowchart of a method for implementing the braking system, according to an embodiment.

FIG. 7 illustrates a flowchart of a method for implementing the braking system, according to an embodiment. The elements provided in the flowchart are illustrative only. Various provided elements may be omitted, additional elements may be added, and/or various elements may be performed in a different order than provided below.

At 701, a user may provide input to the console 100 to indicate the user is about to move the console 100. For example, the user may touch sensors 501 on handle 119. As another example, the user may touch an icon 121 (as part of a graphical user interface) displayed on touchscreen 103 to select a transportation mode (e.g., unlocked for positioning, transport, and/or to store the console). As another example, the user may select an option on a remote control 123 (e.g., push an "unlock" or "move" button). As yet another example, the user may press a button 125 or switch on the console to signal the actuator 201 to engage or release the wheel gear plate 213.

At 703, the brake on the braking caster may be released. For example, when the signal from the sensors 501 is received, actuator 201 may move a plunger rod 205 to lift a pawl gear 233 out of engagement with a wheel gear plate 213.

At 705, an indication to stop console movement may be received. For example, a user may provide an indication to the console 100 to stop movement. In some embodiments, the user may release the handle 119 and therefore, come out of contact with the sensors 501. The absence of user contact may indicate to the console to stop movement. In some embodiments, the user may engage the brakes by pressing icon 121 displayed on touchscreen 103 or by pressing a button (such as "brake" or "lock") on remote control 123. Other user inputs to engage the brakes are also possible.

At 707, the console 100 may implement the brakes on the braking casters 105 to stop the console 100. For example, the actuator 201 may move the plunger rod 205 to engage the pawl gear 233 with the wheel gear plate 213 to stop rotation of the wheel gear plate 213. The outer wheels 217 of the braking caster 105 may slow to a stop through frictional engagement between a brake pad 215 coupled to the wheels 217 and the wheel gear plate 213. The decreasing motion (versus an abrupt stop) between the wheel gear plate 213 and the brake pad 215 may prevent the surgical console 100 from toppling if a user should inadvertently release the console 100 during transport (e.g., if the user trips and releases the handle 119).

In some embodiments, defaulting to a braked caster when the user is not grasping the handle 119 may allow the user to make quick positioning moves for the console by grasping the console handle 119 (which may release the brake), moving the console (e.g., by micropositioning the console a small distance relative to the user near a surgical table), and releasing the handle (to automatically apply the brakes). This may allow a user to quickly reposition and lock a console without having to manually unlock each caster, move the console, and then manually re-lock each caster.

In some embodiments, the surgical console 100 may include one or more processors (e.g., processor 1001). The processor 1001 may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory 1003 coupled to and/or embedded in the processors 1001 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors 1001 implement one or more of its functions via a state machine, analog circuitry, digital circuitry, and/or logic circuitry, the memory 1003 storing the corresponding operational instructions may be embedded within, or external to, the circuitry comprising the state machine, analog circuitry, digital circuitry, and/or logic circuitry. The memory 1003 may store, and the processor 1001 may execute, operational instructions corresponding to at least some of the elements illustrated and described in association with the figures.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A braking system for a console, comprising:
    an actuator;
    a wheel gear plate, wherein the actuator is configured to interact with the wheel gear plate to inhibit rotation of the wheel gear plate;
    a brake pad;
    an outer wheel coupled to the brake pad; and
    a spring washer plate configured to press the wheel gear plate against the brake pad;
    a pawl gear, wherein the actuator is configured to interact with the wheel gear plate to inhibit rotation of the wheel gear plate through the pawl gear, wherein the actuator is coupled to the pawl gear through a plunger rod;
    wherein the outer wheel is coupled to the console through a rotatable stud connection and wherein the plunger rod passes through the stud connection such that the outer wheel is configured to rotate both about a first axis of rotation that is collinear with the plunger rod and rotate about a second axis of rotation that is offset from and rotated approximately 90 degrees from a plunger rod centerline;
    wherein the wheel gear plate is configured to inhibit rotation of the outer wheel through friction between the wheel gear plate and the brake pad when the actuator inhibits rotation of the wheel gear plate.

2. The braking system of claim 1, wherein the actuator is a bi-stable solenoid.

3. The braking system of claim 1, further comprising at least one sensor located on a handle of the console, wherein the at least one sensor is configured to detect a touch from a human user.

4. The braking system of claim 3, wherein the actuator is triggered to inhibit rotation of the wheel gear plate at least partially in response to a signal from the at least one sensor.

5. The braking system of claim 4, wherein the actuator is configured to inhibit rotation of the wheel gear plate unless a touch is being detected through the at least one sensor.

6. The braking system of claim 3, wherein the at least one sensor is a field effect or capacitive sensor.

7. The braking system of claim 1, wherein the spring washer plate is attached to the outer wheel.

8. The braking system of claim 1, further comprising a manual lever coupled to the pawl gear and accessible to a user of the console, such that a user of the console can manually actuate the pawl gear to inhibit rotation of the wheel gear plate through the manual lever independent of the actuator.

9. A method for braking a console, comprising:
  moving an actuator to interact with a wheel gear plate, wherein interaction between the actuator and the wheel gear plate inhibits rotation of the wheel gear plate and wherein the wheel gear plate is configured to inhibit rotation of an outer wheel through friction between the wheel gear plate and a brake pad coupled to the outer wheel when the actuator inhibits rotation of the wheel gear plate;
  receiving a user input indicating the user is about to move the console; and
  moving the actuator to disengage braking on the wheel gear plate;
  wherein moving the actuator to interact with a wheel gear plate comprises the actuator moving a pawl gear to interact with the wheel gear plate, wherein the actuator is coupled to the pawl gear through a plunger rod;
  wherein the outer wheel is coupled to the console through a rotatable stud connection and wherein the plunger rod passes through the stud connection such that the outer wheel is configured to rotate both about a first axis of rotation that is collinear with the plunger rod and rotate about a second axis of rotation that is offset from and rotated approximately 90 degrees from a plunger rod centerline.

10. The method for braking a console of claim 9, wherein receiving user input comprises detecting user contact with at least one sensor on the console.

11. The method for braking a console of claim 9, further comprising receiving an indication to stop the console.

12. The method for braking a console of claim 11, wherein receiving an indication to stop the console comprises not detecting user contact with a sensor on the console.

13. The method for braking a console of claim 10, wherein the actuator is triggered to inhibit rotation of the wheel gear plate at least partially in response to signals from the at least one sensor.

14. The method for braking a console of claim 13, wherein the actuator is configured to inhibit rotation of the wheel gear plate unless a touch is being detected through the at least one sensor.

15. The method for braking a console of claim 10, wherein the at least one sensor is a field effect or capacitive sensor.

16. The method for braking a console of claim 9, wherein a spring washer plate is configured to press the wheel gear plate against the brake pad and wherein the spring washer plate is attached to the outer wheel.

17. A braking system for a console, comprising:
  an actuator;
  a pawl gear coupled to the actuator;
  a wheel gear plate, wherein the pawl gear is configured to interact with the wheel gear plate to inhibit rotation of the wheel gear plate;
  a brake pad coupled to the wheel gear plate;
  an outer wheel; and
  a spring washer plate configured to press the wheel gear plate against the outer wheel;
  at least one sensor located on a handle of the console, wherein the at least one sensor is configured to detect a touch from a human user, and wherein the actuator is triggered to inhibit rotation of the wheel gear plate at least partially in response to a signal from the at least one sensor;
  wherein the wheel gear plate is configured to inhibit rotation of the outer wheel through friction between the brake pad and the outer wheel when the pawl gear inhibits rotation of the wheel gear plate;
  wherein the actuator is coupled to the pawl gear through a plunger rod;
  wherein the outer wheel is coupled to the console through a rotatable stud connection and wherein the plunger rod passes through the stud connection such that the outer wheel is configured to rotate both about a first axis of rotation that is collinear with the plunger rod and rotate about a second axis of rotation that is offset from and rotated approximately 90 degrees from a plunger rod centerline.

* * * * *